United States Patent
Laghi

(10) Patent No.: US 6,706,075 B1
(45) Date of Patent: Mar. 16, 2004

(54) DYNAMIC PROSTHETIC FOOT WITH MULTIPLE LOAD POINTS HAVING SOLE ONLY

(76) Inventor: Aldo A. Laghi, 14410 Eagle Point Dr., Clearwater, FL (US) 33762

( * ) Notice: Subject to any disclaimer, the term of this patent is extended or adjusted under 35 U.S.C. 154(b) by 49 days.

(21) Appl. No.: 10/064,843

(22) Filed: Aug. 22, 2002

(51) Int. Cl.$^7$ .............................. A61F 2/66; A61F 2/68
(52) U.S. Cl. ............................ 623/52; 623/55; 623/53
(58) Field of Search ........................... 623/53, 54–56, 623/47, 49, 52

(56) References Cited

U.S. PATENT DOCUMENTS

| | | | | |
|---|---|---|---|---|
| 4,645,509 A | * | 2/1987 | Poggi et al. ................. | 623/55 |
| 5,037,444 A | * | 8/1991 | Phillips ........................ | 623/55 |
| 5,062,859 A | * | 11/1991 | Naeder ........................ | 623/55 |
| 5,116,383 A | * | 5/1992 | Shorter et al. ................ | 623/49 |
| 5,139,525 A | * | 8/1992 | Kristinsson ................. | 623/55 |
| 5,653,767 A | * | 8/1997 | Allen et al. .................. | 623/52 |
| 5,695,527 A | * | 12/1997 | Allen ........................... | 623/55 |
| 5,776,205 A | * | 7/1998 | Phillips ....................... | 623/55 |
| 5,944,760 A | * | 8/1999 | Christensen ................. | 623/55 |
| 6,165,227 A | * | 12/2000 | Phillips ....................... | 623/53 |
| 6,197,068 B1 | * | 3/2001 | Christensen ................. | 623/55 |
| 6,280,479 B1 | * | 8/2001 | Phillips ....................... | 623/52 |
| 6,514,293 B1 | * | 2/2003 | Jang et al. .................... | 623/55 |
| 6,602,295 B1 | * | 8/2003 | Doddroe et al. ............. | 623/55 |
| 2002/0013628 A1 | * | 1/2002 | Harris .......................... | 623/55 |
| 2003/0009238 A1 | * | 1/2003 | Whayne ....................... | 623/32 |

\* cited by examiner

*Primary Examiner*—Corrine McDermott
*Assistant Examiner*—Alvin Stewart
(74) *Attorney, Agent, or Firm*—Ronald E. Smith; Smith & Hopen, P.A.

(57) ABSTRACT

A dynamic prosthetic foot having multiple load points includes a sole only. A longitudinally-extending slot divides the heel end of the sole into a lateral heel member and a medial heel member. A heel end of the lateral heel member is formed by a return bend that terminates in an upwardly turned straight pylon support that is normal to the sole. The medial pylon support has the same construction but has less thickness and strength and therefore more flexibility than the lateral pylon support. In a second embodiment, an elongate pylon supplants each pylon support. The split heel structure provides a prosthetic foot having enhanced heel elasticity.

15 Claims, 4 Drawing Sheets

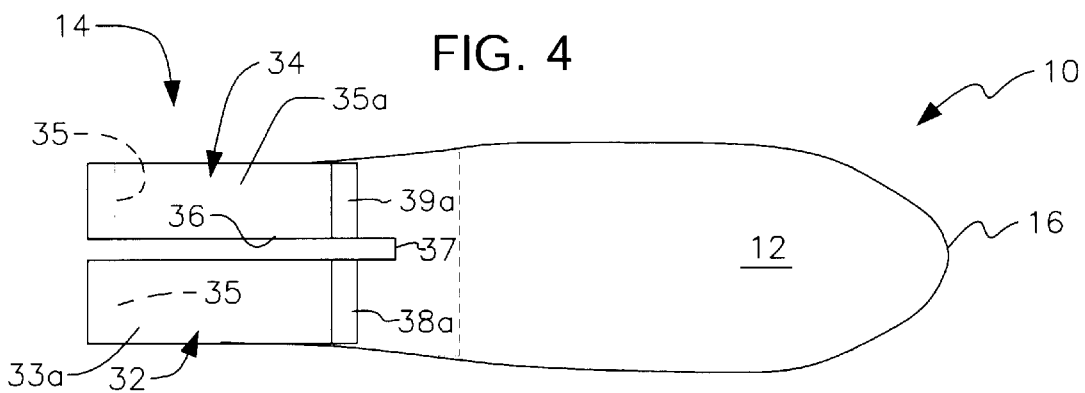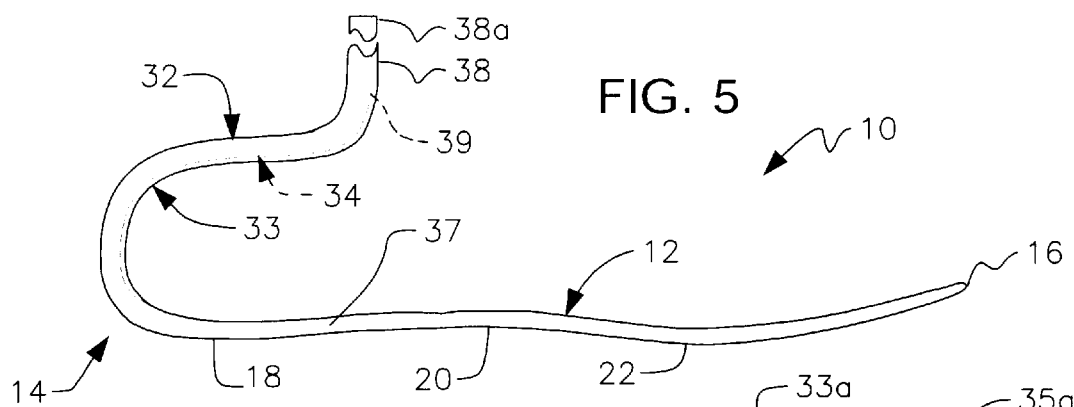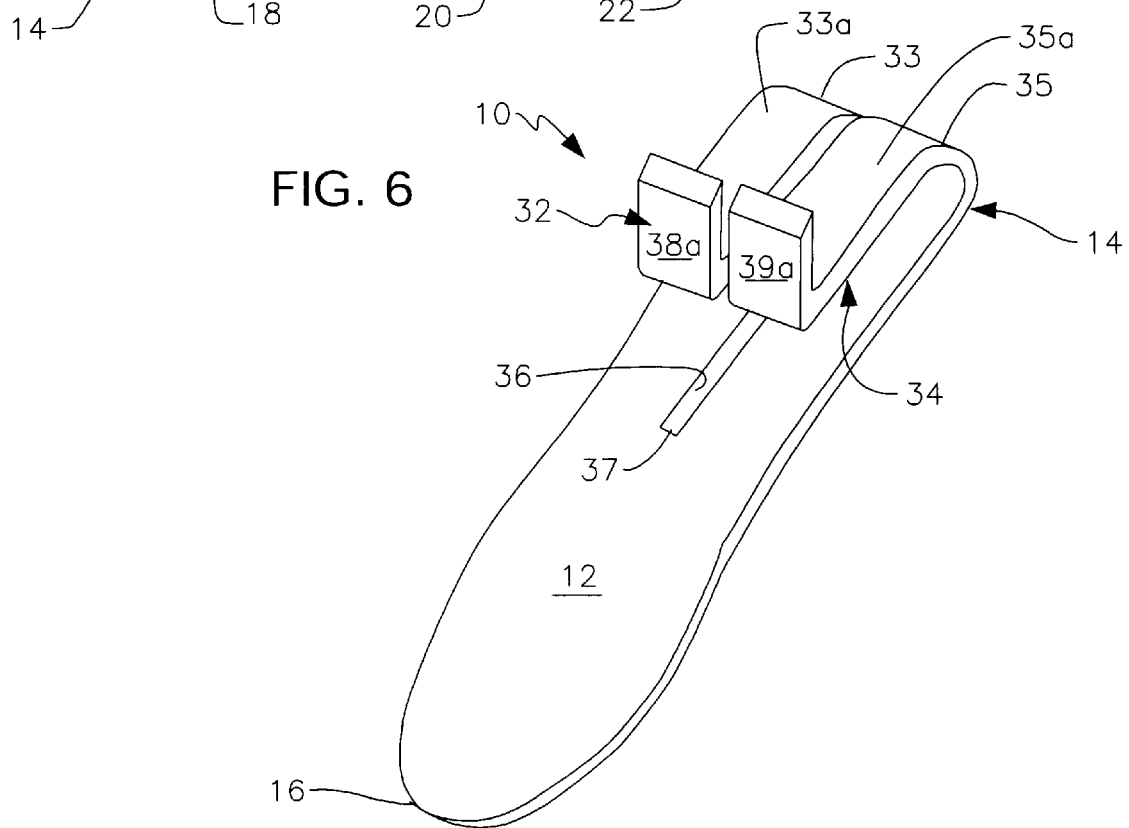

FIG. 7
FIG. 8
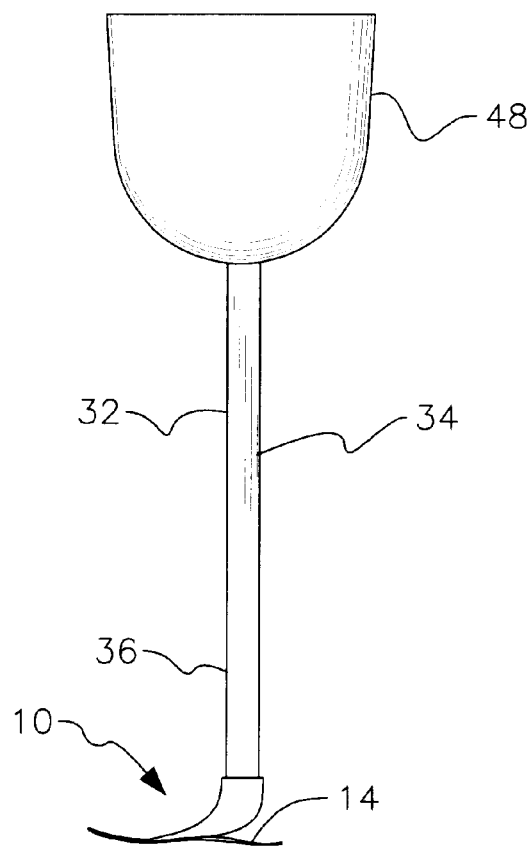
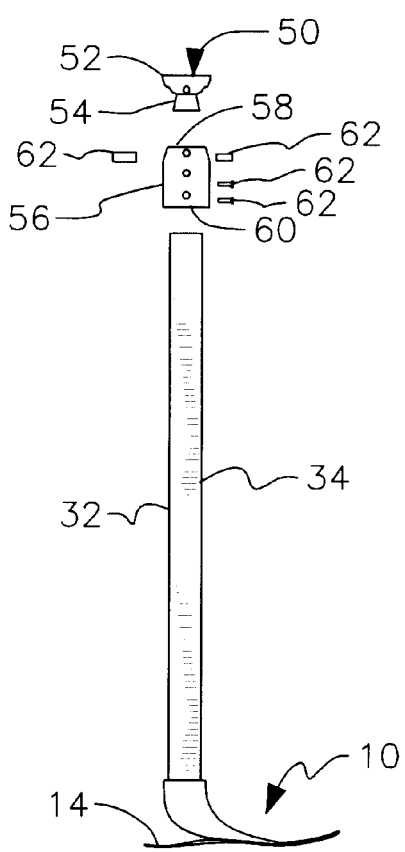

DYNAMIC PROSTHETIC FOOT WITH MULTIPLE LOAD POINTS HAVING SOLE ONLY

BACKGROUND OF INVENTION

1. Field of the Invention

This invention relates, generally, to the art of prosthetics. More particularly, it relates to improvements in prosthetic feet.

2. Description of the Prior Art

During normal ambulation, the first part of a foot to contact the ground is the free end of the heel. This initial contact between heel and ground is known as the "heel strike." The free end of the heel is soft and thus cushions the heel strike to at least some extent. The hard bottom of the heel is the next part of the foot to strike the ground; its hardness allows it to support the entire weight of the body. The foot continues to rotate in the well-known way until the toes "push off" at the end of a step.

Early prosthetic feet were quite rigid and provided little or no cushion to the impact on the ground at the moment of "heel strike" and little or no elastic response at "push off." The shock of impact was thus transmitted directly to the skeletal structure of the user, and the lack of elastic response forced an unnatural gait.

Perhaps the earliest prosthetic foot that provided an elastic response at heel strike and push off is disclosed in U.S. Pat. No. 4,547,913 to Phillips, assigned to Flex Foot, Inc. Multiple versions of that device have been developed. The original version is formed of a carbon fiber epoxy matrix consisting of a one-piece combination pylon upper and a one-piece sole. Mechanical fasteners interconnect the upper and the sole. In a second embodiment, the pylon is a round hollow tube and is connected by mechanical fasteners to a rectangular-shaped upper. A third version is like the first except that a standard Sach® foot adapter is employed to connect a standard prosthetic pylon. A fourth version is like the third but has a slightly different geometry. In a fifth version, an elastomeric glue connects the upper and the sole. In additional embodiments, leaf springs or hydraulic cylinders are incorporated into the prosthetic foot.

Although the developments in the art since the mid 1980s have significantly advanced the technology of prosthetic feet, the known prosthetic feet still provide little or no heel elasticity in a direction parallel to the ground. Instead, they provide elastic response in a vertical plane. Thus, although the impact at heel strike is reduced vis a Vis the pre-1980's prosthetic feet, the reduced impact is transmitted vertically to the skeletal structure of the user, and the elastic response in a vertical plane causes a four to six millimeter bounce at heel strike. This vertical response causes an unnatural walk because a healthy human heel is soft at the back or free end where heel strike occurs and is hard on the bottom so that it can support the entire weight of the body. Thus, the normal gait of a human includes a rolling motion as the back of the heel strikes the ground; there is no vertical motion causing the heel to bounce upon ground impact. Accordingly, there remains a need for a prosthetic foot that provides substantial heel elasticity in a direction parallel to the ground.

A healthy human foot rolls on the lateral part of the foot during ambulation. The medial part of the foot provides a cushion and the force required at push off. Thus, there is a smooth transition from heel strike to push off, with no vertical dynamic response of the type that could cause the foot to bounce. Prosthetic feet, however, do not provide a smooth transition from heel strike to push off. This lack of a smooth transition produces what is known in the industry as a "flat spot." The presence of a flat spot between heel strike and push off produces an unnatural gait.

More particularly, the dynamic response is primarily vertical at the heel and the toe of a prosthetic foot. There is little or no component of the dynamic response in a horizontal plane as present in a healthy natural foot. The absence of dynamic response in a horizontal plane results in a step like motion going from an elastic vertical motion at heel strike to little or no support at mid-stance (the flat spot), and then again to an elastic vertical motion at push off.

There is a need, therefore, for a prosthetic foot having a dynamic response in a horizontal plane during heel strike, that provides a smooth transition between heel strike and push off to eliminate the flat spot, and that provides a dynamic response in a horizontal plane during push off.

The human foot provides a more rigid support laterally than medially. This design is advantageous because when an instability occurs, the weight of the person shifts from the rigid outer or lateral edge of the foot to the less rigid inner or medial edge. In this way, the prosthetic foot takes advantage of the presence of the natural foot, i.e., the lateral-to-medial motion experienced at the moment of an instability shifts additional support duties to the natural foot. One major drawback of the heretofore known prosthetic feet is the fact that such feet provide an exactly vertical response during ambulation with no component toward the medial section of the foot. Thus, if an instability in one foot urges the person to fall away from the natural foot, there is no shift of weight toward the medial part of the prosthetic foot as would occur in a natural foot, and the likelihood of a fall is substantially increased.

A prosthetic foot is therefore needed that has differentiated medial and lateral stiffness so that it can respond to instabilities in much the same way as a natural foot.

However, in view of the prior art considered as a whole at the time the present invention was made, it was not obvious to those of ordinary skill in the pertinent art how the identified needs could be fulfilled.

SUMMARY OF INVENTION

The long-standing but heretofore unfulfilled need for a dynamic prosthetic foot is now met by a new, useful, and nonobvious prosthetic foot that provides multiple load points and which has a sole only, there being no upper section. The sole includes a heel end and a toe end.

A slot substantially coincident with a longitudinal axis of the dynamic prosthetic foot is formed in the heel end of the sole, dividing the heel into a lateral heel member and a medial heel member. The slot extends from the heel end to a preselected point in the sole. In a first embodiment, the foot includes a lateral pylon support formed integrally with the lateral heel member and a medial pylon support formed integrally with the medial heel member. The lateral pylon support and medial pylon support are in transverse alignment with one another.

The lateral heel member is formed by a return bend formed in the sole at the heel end thereof. The lateral heel member includes a straight section substantially parallel to the sole that extends toward the toe of the foot. The straight section terminates in a ninety degree bend formed integrally with the straight section. The ninety degree bend extends upwardly and forms a lateral pylon support disposed normal to the sole.

The medial heel member is also formed by a return bend formed in the sole at the heel end thereof. The medial heel member includes a straight section substantially parallel to the sole that extends toward the toe of the foot. The straight section terminates in a ninety degree bend formed integrally with the straight section. The ninety degree bend extends upwardly and forms a medial pylon support disposed normal to the sole.

This novel split return bend heel structure provides heel elasticity. The return bend structure also strikes the ground in a way that facilitates normal ambulation.

A lateral pylon connector adapted to receive a lateral pylon of a prosthetic leg is secured to a trailing end of the lateral pylon support. A medial pylon connector adapted to receive a medial pylon of a prosthetic leg is secured to a trailing end of the medial pylon support.

Forces acting on the lateral pylon connector are substantially confined to the lateral pylon support and forces acting on the medial pylon connector are substantially confined to the medial pylon support. Moreover, forces acting on the lateral pylon connector are similar to the forces acting on a fibula of a natural leg and forces acting on the medial pylon connector are similar to the forces acting on a tibia of a natural leg.

The lateral pylon support has a greater thickness and less flexibility than the medial pylon support. The greater thickness imparts greater strength so that forces applied to the lateral pylon support and the medial pylon support are transferred more to the medial pylon support than to the lateral pylon support, thereby mimicking the reaction of a natural foot to forces applied thereto.

In a second embodiment, each pylon support is elongated so that it becomes a pylon, thereby eliminating the need for the pylon connectors. Each pylon is about twenty inches (20") in length and is cut to length as required by a prosthetist at the time a patient is fitted with the novel prosthetic foot.

In both embodiments, the sole has a first convexity formed in the heel end that performs the function of the bottom of a natural heel. The sole has a concavity, performing the function of a natural arch, that is longitudinally spaced from the first convexity. A second convexity that performs the function of the ball of a natural foot is longitudinally spaced from the concavity.

An important object of this invention is to provide a dynamic prosthetic foot having heel elasticity in a direction parallel to the ground.

Another important object is to provide a dynamic prosthetic foot having a smooth transition from heel strike to push off.

Yet another object is to provide a dynamic prosthetic foot having differentiated medial and lateral stiffness so that an instability tends to shift weight from the lateral edge of the prosthetic foot to the medial edge thereof, just as in a natural foot.

Another important object is to provide a prosthetic foot having a heel divided into a lateral part and a medial part and where the flexing of the medial part exceeds the flexing of the lateral part.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 4 is a top plan view of a second embodiment of the novel prosthetic foot with multiple load points and a sole only having elongate pylons that supplant the truncate pylon supports of the first embodiment;

FIG. 5 is a side elevational view of said FIG. 4 embodiment;

FIG. 6 is a perspective view of said FIG. 4 embodiment;

FIG. 7 is a perspective view of the elongate pylons embodiment when attached to a prosthetic socket;

FIG. 8 is a perspective view of the elongate pylons embodiment and further depicting connector means, in exploded form, for connecting said elongate pylons to a socket;

DETAILED DESCRIPTION

Figure 1:
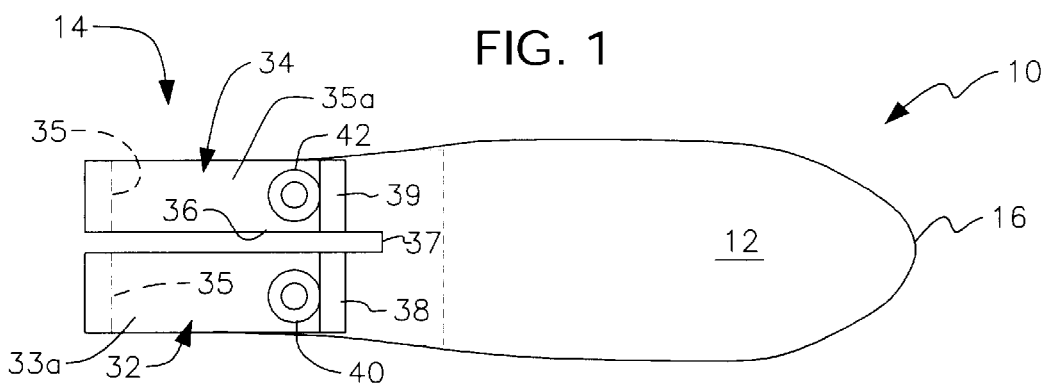
FIG. 1 is a top plan view of a first embodiment of the novel prosthetic foot with multiple load points and a sole only having truncate pylon supports.
Figure 2:
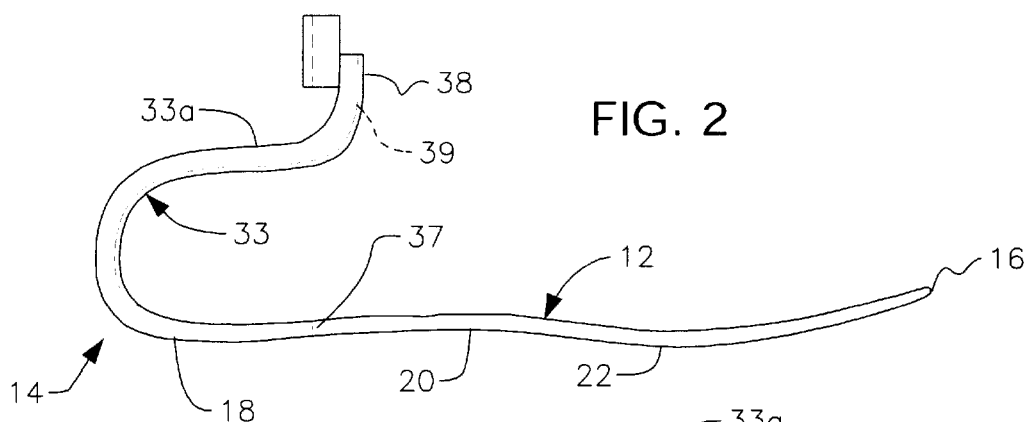
FIG. 2 is a side elevational view of said FIG. 1 embodiment.
Figure 3:
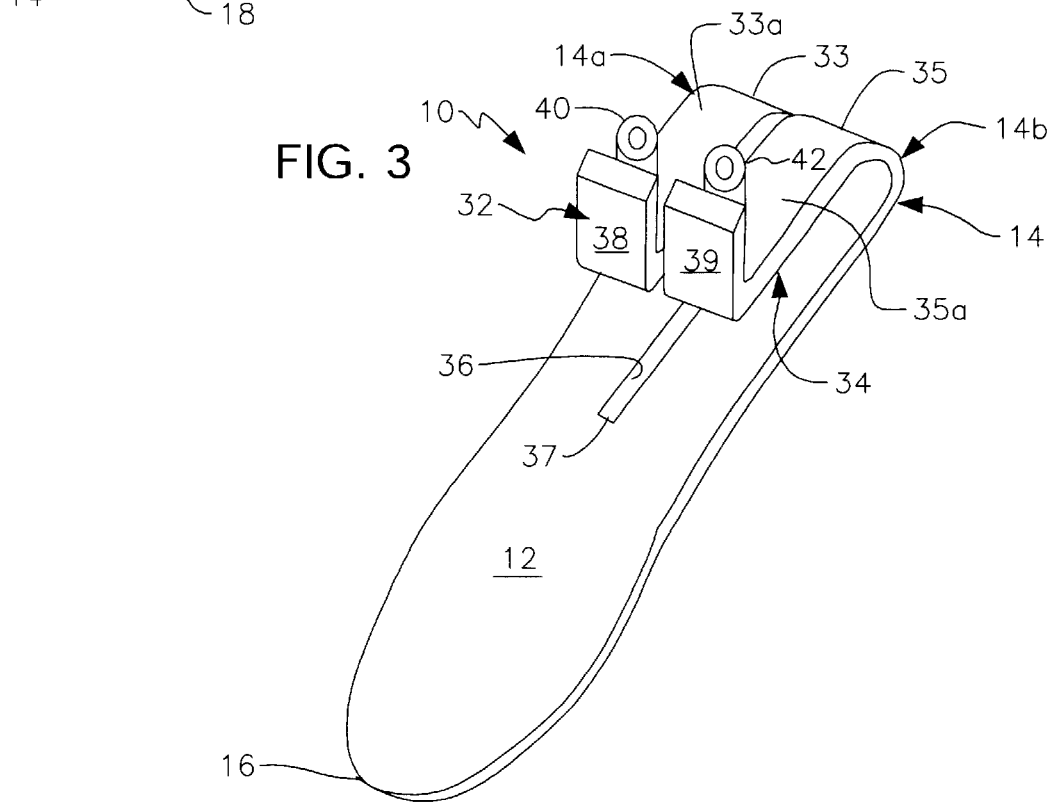
FIG. 3 is a perspective view of said FIG. 1 embodiment.

Referring to FIGS. 1–3, it will there be seen that the reference numeral 10 denotes a first illustrative embodiment of the novel dynamic prosthetic foot having multiple load points and a sole only, there being no upper section that overlies the sole.

Prosthetic foot 10 includes sole 12 having a heel end 14 and a toe end 16. Relative to a horizontal support surface, as best understood in connection with FIG. 2, sole 12 includes first convexity 18 that performs the function of the bottom of a natural heel, concavity 20 that performs the function of a natural arch, and second convexity 22 that performs the function of the ball of a natural foot.

Sole 12 includes a pair of heel members 32, 34 that are separated from one another by longitudinally extending slot 36. Slot 36 has a heel end in open communication with heel end 14 of sole 12 as best depicted in FIG. 1.

In a first embodiment, dynamic prosthetic foot 10 includes lateral pylon support 38 formed integrally with lateral heel member 32 and medial pylon support 39 formed integrally with medial heel member 34. Lateral pylon support 38 and medial pylon support 39 are in transverse alignment with one another.

Lateral heel member 32 is formed by return bend 33 formed in sole 12 at heel end 14 thereof. Lateral heel member 32 includes straight section 33a substantially parallel to sole 12 that extends toward toe 16 of foot 10. Straight section 33a terminates in a ninety degree bend formed integrally with said straight section. The ninety degree bend extends upwardly and forms lateral pylon support 38 that is disposed normal to sole 12.

Medial heel member 34 is formed by return bend 35 formed in sole 12 at heel end 14 thereof. Medial heel member 34 includes straight section 35a substantially parallel to sole 12 that extends toward toe 16 of foot 10. The straight section terminates in a ninety degree bend formed integrally with the straight section. The ninety degree bend extends upwardly and forms medial pylon support 39 that is disposed normal to sole 12.

Toe end 37 of slot 36 terminates at a preselected location which may be described as being just slightly to the toe side of lateral and medial pylon supports 38, 39, respectively. Point 37 may also be described as being positioned at an inflection point where first convexity 18 meets concavity 20, i.e., where the upward slope of the toe end of said convexity meets the downward slope of the heel end of concavity 20.

Lateral pylon support 38 has a greater thickness than medial pylon support 39. Accordingly, it flexes less and absorbs more forces. The greater thickness of lateral pylon support 38 ensures that instabilities appearing on foot 10 will be shifted in a medial direction, just like a natural foot. Slot 36 enables lateral pylon support 38 to respond to instabilities substantially independently of medial pylon support 39, and vice versa.

The same may be said for lateral heel member 32 and lateral heel member 34, i.e. slot 36 enables such heel members to respond somewhat independently to forces appearing on heel 14.

Tubular pylon connector 40 is secured to the heel side of lateral pylon support 38, centrally thereof, and tubular pylon connector 42 is secured to the heel side of medial pylon support 39, centrally thereof. In this first embodiment, a lateral pylon, not shown, is received within pylon connector 40 and a medial pylon, not shown, is received within pylon connector 42 when dynamic prosthetic foot 10 is engaged to a prosthetic leg that includes said unillustrated pylons.

Heel 14 provides a dynamic response in the horizontal plane during heel strike. This eliminates the bounce caused by the dynamic response in the vertical plane of prior art prosthetic feet, helps eliminate the mid stance flat spot, and provides a rolling transition from heel strike to mid stance to push off.

Moreover, the bifurcated construction of pylon supports 38, 39 and the greater thickness of lateral pylon support 38 vis a vis medial pylon support 39 enhances the stability of the user because said greater thickness and hence greater strength and less flexibility serve to shift the weight of the user toward the medial side of the foot and thus harnesses the stabilizing power of the natural foot that opposes the prosthetic foot.

Medial pylon support 38 flexes or "gives" more than lateral pylon support 39 when a user walks in a normal gait because said medial pylon support 39 has less strength and more flexibility than lateral pylon support 38. This structure further ensures that instabilities appearing on the unillustrated prosthetic leg pylons will be shifted primarily from lateral pylon support 38 to medial pylon support 39. Such re-distribution of forces enables the natural opposed leg to become involved in restoring balance when external forces threaten such balance.

In the second embodiment of the invention, depicted in FIGS. 4–6, pylon supports 38 and 39 are obviated and supplanted by elongate pylons 38a, 39a that are about twenty inches (20") in length. Said elongate pylons are cut to size by a prosthetist when a patient is fitted with a prosthetic foot. Elongate pylons 38a, 39a eliminate the need for pylon connectors 40, 42 of the first embodiment. Lateral elongate pylon 38a is thicker and less flexible that medial elongate pylon 39a so that the features provided by the structure of the first embodiment are also provided by the structure of the second embodiment.

FIG. 7 depicts novel dynamic prosthetic foot 10 when equipped with elongate pylons 38a, 39a.

After pylons 38a, 39a have been cut to a desired length, the prosthetist has several options by which the pylons may be connected to prosthetic socket 48. Pylons 38a, 39a may be laminated into prosthetic socket 48 as illustrated in said FIG. 7. This forms a permanent connection between pylons 38a, 39a and socket 48.

A second option includes the use of a commercially available pyramid connector 50 as depicted in FIG. 8. Such pyramid connectors have been in use for fifty or so years. Pyramid connector 50 includes upper part 52 and lower part 54 that depends from the upper part. Upper part 52 is attached to the lowermost or distal end of socket 48. A hollow pyramid-receiving connector 56 has an open upper end 58 that receives lower part 54 of pyramid connector 50 and an open lower end 60 that receives the respective uppermost ends of pylons 38a, 39a. Lower end 54 of pyramid connector 50 and the respective upper ends of pylons 38a, 39a are captured in said hollow pyramid-receiving connector 56 by a plurality of set screws and other suitable fastening means, collectively denoted 62.

Pyramid connector 52 and pyramid-receiving connector 56 are employed to enable adjustment of the angle of pylons 38a, 39a so that prosthetic foot 10 falls in the correct medial/lateral and anterior/posterior planes, as perhaps best understood by making reference to FIG. 8.

A third option available to the prosthetist after cutting pylons 38a, 39a to their correct length is to laminate the pylons to an unillustrated component and to attach that component to the socket.

Figure 9A:
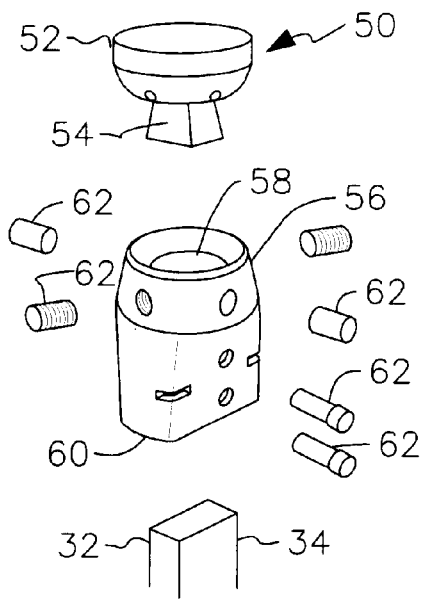
FIG. 9A is an exploded first perspective view of said connector means.
Figure 9B:
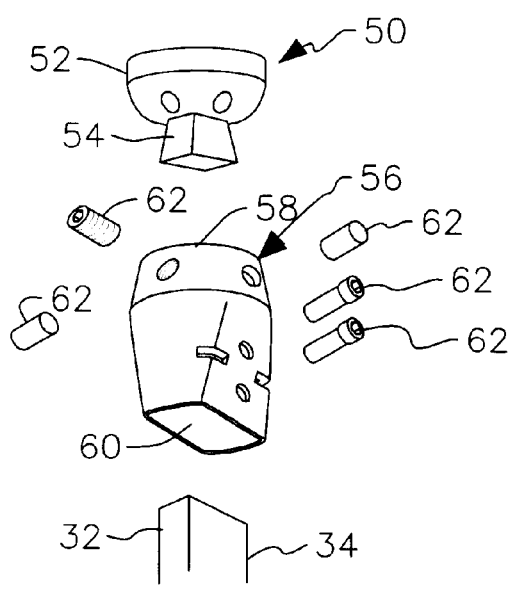
FIG. 9B is an exploded second perspective view of said connector means.
Figure 9C:
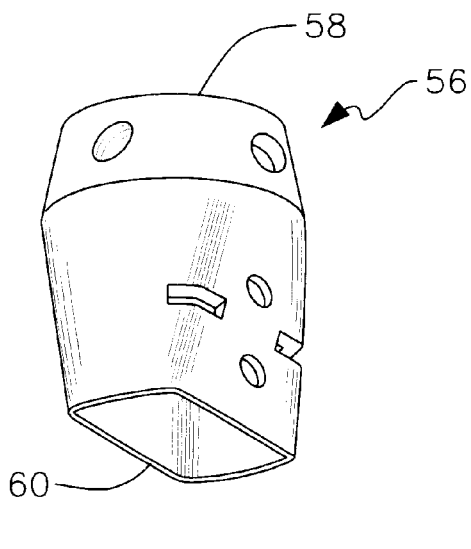
FIG. 9C is a first perspective view of a pyramid-receiving connector.
Figure 9D:
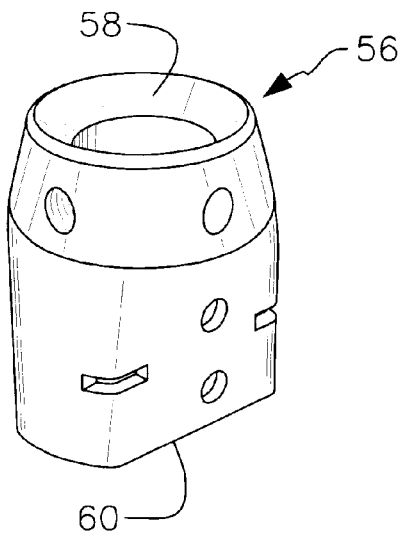
FIG. 9D is a second perspective view of said pyramid-receiving connector.

FIGS. 9A and 9B provide a more detailed perspective view of pyramid connector 50 and pyramid-receiving connector 56. FIGS. 9C and 9D provide a more detailed perspective view of pyramid-receiving connector 56.

In the first embodiment, the thickness of pylon support 38 is substantially different than the thickness of pylon support 39 and in the second embodiment, the thickness of elongate pylon 38a is substantially different than the thickness of elongate pylon support 39a to provide a controlled elastic response. More specifically, the greater thickness of lateral pylon support 38 or lateral elongate pylon 38a shifts loads to the medial section of foot 10. This provides the function of eliminating the flat spot of earlier prosthetic feet because such construction provides a smooth transition from heel strike to push off. Moreover, the bifurcated construction of pylon supports 38, 39 (FIGS. 1–3) or pylons 38a, 39a (FIGS. 4–6) and the greater-thickness of lateral pylon support 38 (FIGS. 1–3) or elongate pylon 38a (FIGS. 4–6) enhance the stability of the user because said greater thickness serves to shift the weight of the user toward the medial side of the foot and thus harnesses the stabilizing power of the sound foot that opposes the prosthetic foot.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,
What is claimed is:

1. A dynamic prosthetic foot having multiple load points, comprising:

a sole having a heel end and a toe end;

a slot formed in said heel end of said sole, said slot substantially coincident with a longitudinal axis of said dynamic prosthetic foot and said slot extending from said heel end of said sole to a preselected point in said sole;

said slot dividing said heel end into a lateral heel member and a medial heel member, said lateral heel member and said medial heel member being separated from one another by said slot;

said lateral heel member including a lateral pylon support and said medial heel member including a medial pylon support;

said lateral heel member being formed by a return bend formed in said sole at said heel end thereof and said return bend terminating in a ninety degree upwardly turned bend to form said lateral pylon support, said lateral pylon support being disposed normal to said sole;

said medial heel member being formed by a return bend formed in said sole at said heel end thereof and said return bend terminating in a ninety degree upwardly turned bend to form said medial pylon support, said medial pylon support being disposed normal to said sole;

a lateral pylon connector secured to a trailing end of said lateral pylon support, said lateral pylon connector adapted to receive a lateral pylon of a prosthetic leg;

a medial pylon connector secured to a trailing end of said medial pylon support, said medial pylon connector adapted to receive a medial pylon of a prosthetic leg;

whereby forces acting on said lateral pylon connector are substantially confined to said lateral pylon support and forces acting on said medial pylon connector are substantially confined to said medial pylon support; and whereby said foot exhibits enhanced heel elasticity.

2. The dynamic prosthetic foot of claim 1, wherein said lateral pylon support has a greater thickness, greater strength, and less flexibility than said medial pylon support, so that forces applied to said lateral pylon support and said medial pylon support are transferred more to said medial pylon support than to said lateral pylon support, thereby mimicking the reaction of a natural foot to forces applied thereto.

3. The dynamic prosthetic foot of claim 1, wherein said sole has a first convexity formed in said heel end that performs the function of the bottom of a natural heel.

4. The dynamic prosthetic foot of claim 3, wherein said sole has a concavity longitudinally spaced from said first convexity, said concavity performing the function of a natural arch.

5. The dynamic prosthetic foot of claim 4, wherein said sole has a second convexity longitudinally spaced from said concavity, said second concavity performing the function of the ball of a natural foot.

6. The dynamic prosthetic foot of claim 5, wherein said preselected point is an inflection point where an upward slope of said first convexity meets a downward slope of said concavity.

7. A dynamic prosthetic foot having multiple load points, comprising:

a sole having a heel end and a toe end;

a slot formed in said heel end of said sole, said slot substantially coincident with a longitudinal axis of said dynamic prosthetic foot and said slot extending from said heel end of said sole to a preselected point in said sole;

said slot dividing said heel end into a lateral heel member and a medial heel member, said lateral heel member and said medial heel member being separated from one another by said slot;

said lateral heel member including an elongate lateral pylon and said medial heel member including an elongate medial pylon;

said lateral heel member being formed by a return bend formed in said sole at said heel end thereof and said return bend terminating in a ninety degree upwardly turned bend to form said elongate lateral pylon, said elongate lateral pylon being disposed normal to said sole;

said medial heel member being formed by a return bend formed in said sole at said heel end thereof and said return bend terminating in a ninety degree upwardly turned bend to form said elongate medial pylon, said elongate medial pylon being disposed normal to said sole;

whereby forces acting on said elongate lateral pylon are substantially confined to said elongate lateral pylon and forces acting on said elongate medial pylon are substantially confined to said elongate medial pylon; and whereby said foot exhibits enhanced heel elasticity.

8. The dynamic prosthetic foot of claim 7, wherein said elongate lateral pylon has a greater thickness, greater strength, and less flexibility than said elongate medial pylon, so that forces applied to said elongate lateral pylon and said elongate medial pylon are transferred more to said elongate medial pylon than to said elongate lateral pylon, thereby mimicking the reaction of a natural foot, to forces applied thereto.

9. The dynamic prosthetic foot of claim 7, wherein said sole has a first convexity formed in said heel end that performs the function of the bottom of a natural heel.

10. The dynamic prosthetic foot of claim 9, wherein said sole has a concavity longitudinally spaced from said first convexity, said concavity performing the function of a natural arch.

11. The dynamic prosthetic foot of claim 10, wherein said sole has a second convexity longitudinally spaced from said concavity, said second concavity performing the function of the ball of a natural foot.

12. The dynamic prosthetic foot of claim 11, wherein said preselected point is an inflection point where an upward slope of said first convexity meets a downward slope of said concavity.

13. The dynamic prosthetic foot of claim 7, wherein said lateral and medial pylons are adapted to be laminated at respective uppermost ends thereof to a prosthetic socket.

14. The dynamic prosthetic foot of claim 7, wherein said lateral and medial pylons are adapted to be connected at respective uppermost ends thereof to a connector member and wherein said connector member is laminated to a prosthetic socket.

15. The dynamic prosthetic foot of claim 7, wherein said lateral and medial pylons are adapted to be connected at respective uppermost ends thereof to a pyramid-receiving connector that engages a pyramid that depends from said prosthetic socket.

* * * * *